United States Patent [19]

Coons, III

[11] Patent Number: 5,195,313
[45] Date of Patent: Mar. 23, 1993

[54] METHOD FOR EVALUATING ENTANGLED YARN

[75] Inventor: Andrew M. Coons, III, Anderson, S.C.

[73] Assignee: BASF Corporation, Parsippany, N.J.

[21] Appl. No.: 821,258

[22] Filed: Jan. 10, 1992

Related U.S. Application Data

[63] Continuation of Ser. No. 619,266, Nov. 28, 1990, abandoned.

[51] Int. Cl.⁵ .......................... D02G 1/16; D02J 1/08; D01H 13/26
[52] U.S. Cl. .................................. 57/264; 57/206; 57/350; 28/271; 28/274
[58] Field of Search .................... 57/206, 208–209, 57/264, 330, 350; 28/271, 227, 274

[56] References Cited

U.S. PATENT DOCUMENTS

| | | | |
|---|---|---|---|
| 2,985,995 | 5/1961 | Bunting, Jr. et al. | 57/140 |
| 3,110,151 | 11/1963 | Bunting, Jr. et al. | 57/157 |
| 3,115,691 | 12/1963 | Bunting, Jr. et al. | 28/1 |
| 3,140,604 | 7/1964 | Bernet | 28/227 X |
| 3,426,406 | 2/1969 | McCutchan, Jr. | 28/1 |
| 3,474,510 | 10/1969 | Torsellini | 28/1 |
| 3,563,021 | 2/1971 | Gray | 57/140 |
| 3,731,069 | 5/1973 | Goto et al. | 28/227 X |
| 3,846,968 | 11/1974 | Sheehan et al. | 57/34 B |
| 3,908,248 | 9/1975 | Schmid et al. | 28/1.4 |
| 4,064,686 | 12/1977 | Whitted et al. | 57/140 J |
| 4,070,815 | 1/1978 | Negishi et al. | 28/274 X |
| 4,115,988 | 8/1978 | Nakagawa et al. | 57/206 X |
| 4,152,885 | 5/1979 | Cox | 57/207 |
| 4,152,886 | 5/1979 | Nelson | 57/208 |
| 4,223,520 | 9/1980 | Whitted et al. | 57/350 |
| 4,311,000 | 1/1982 | London et al. | 57/208 X |
| 4,345,425 | 8/1992 | Negishi et al. | 28/274 X |
| 4,570,312 | 2/1986 | Whitener, Jr. | 28/271 |
| 4,631,791 | 12/1986 | Symon | 57/350 X |
| 4,667,380 | 5/1987 | Symon | 57/350 X |
| 4,697,317 | 10/1987 | Nelson | 28/258 |
| 4,736,578 | 4/1988 | Shaffer | 57/209 X |
| 4,841,606 | 6/1989 | Coons, III | 28/274 |
| 4,894,894 | 1/1990 | Coons, III et al. | 28/220 |

Primary Examiner—John M. Jillions
Assistant Examiner—William Stryjewski

[57] ABSTRACT

Described is a method for quantifying interlacing characteristics of multifilamentary yarn, having nodes of a length and a width comprising, (a) measuring the length (L) of at least one node, (b) measuring the width (W) of at least each node measured in step (a) and (c) determining the value of the node harshness from the ratio of L to W for each node measured in step (a).

4 Claims, 3 Drawing Sheets

METHOD FOR EVALUATING ENTANGLED YARN

This is a continuation of copending application Ser. No. 07/619,266 filed on Nov. 28, 1990, abandoned.

BACKGROUND OF THE INVENTION

This invention relates generally to methods of evaluating fibrous synthetic polymers. More specifically, the invention relates to a method for quantifying nodal characteristics in fluid entangled filaments.

In the synthetic fiber industry, it has long been recognized that yarn bundles should be coherent for processing at high rates of speed. Initially, such yarns were made by twisting. But twisted yarn is expensive and complicated to produce.

Responding to the need for inexpensive coherent yarn filaments, fiber manufacturers discovered that yarns could be interlaced. Later it was recognized that interlacing was a means to mix fibers of different types, such as color or dye affinity. U.S. Pat. No. 3,846,968 to Sheehan et al. demonstrates a mixed fiber application of interlacing.

An interlaced yarn is characterized by points of entanglement, called nodes, which are separated by spaces of unentangled filaments. Commonly, individual yarn filaments are interlaced by exposing the filament bundle to a localized fluid jet. U.S. Pat. No. 2,985,995 and 3,110,151, both to Bunting, Jr., et al. describe several methods of inducing interlacing by fluid impingement. These patents show what is referred to herein as a hard tight node (see U.S. Pat. No. 2,985,995, FIG. 25). One such interlacer has openings at various angles of a rotary wheel design. The rotary wheel turns with the yarn and creates an even spacing which can result in patterning of yarns having different color components in the final product. For the purposes of the present invention, "even" spacing means essentially equal distance between nodes. The Bunting, Jr., et al. patents teach that more than one interlacer can be used in series and that the spacing of nodes can be varied between random and periodic by adjusting the fluid temperature, processing speed and finish. To accomplish these objectives, the Bunting, Jr., et al. interlacers are designed for free movement of the filaments in the yarn passage.

Many methods for interlacing filaments refer to the node spacing as random or irregular. However, for certain applications of yarns made from two or more contrasting filaments with, for example, different dye affinities or which are precolored differently, for example heather carpets, as presented in U.S. Pat. Nos. 4,223,520 to Whitted et al., 4,570,312 to Whitener, Jr., and 4,697,317 to Nelson, it is important that the nodes be regularly spaced. Otherwise, the nodeless gaps show up in the carpet as stria or short sections. A series of stria can appear as a streak, like the dashes in the road form a center line. As used herein, "regular" nodes are nodes with unequal spacing having no gaps between them above 6 cms.

There are methods of periodically interlacing filaments. As used herein, a periodically interlaced filament is one having internodal spacing which is even or regular. For example, U.S. Pat. No. 3,115,691 to Bunting, Jr., et al. describes a single interlacing apparatus having two jet streams therein. According to the patent, the arrangement results in a greater degree of entanglement.

U.S. Pat. No. 3,426,406 to McCutchan, Jr. describes an interlacing apparatus designed to overcome randomness and streaking. At least one pair of opposed fluid conduits having a common longitudinal axis which intercepts and is perpendicular to the axis of an elliptical yarn passageway achieves the objective.

U.S. Pat. No. 3,474,510 to Torsellini describes a method to overcome randomness in the prior devices by exposing the yarn moving under tension to fluid pulses. The pulses occur at constant time intervals and act on the yarn from different directions.

U.S. Pat. No. 3,563,021 to Gray describes the use of cooperating tandem jets to achieve a uniformly interlaced yarn. The oscillation of the filament bundle produced by the first jet acts to traverse the yarn between the orifices of the other jet.

U.S. Pat. Nos. 4,064,686 and 4,223,520, both to Whitted et al., are directed to an interlaced yarn having alternatingly twisted nodes. That is, one node is twisted counterclockwise, the next is twisted clockwise and so on. This is achieved by using diametrically opposed fluid passages in the entangling apparatus. The stretching in the interlacing apparatus can be changed by adjusting the tension so that some portions are stretched more than others and, upon dyeing, cause a color differential.

In addition, there are several methods for producing novelty yarns by various entangling procedures. One such yarn is disclosed in U.S Pat. No. 3,846,968 to Sheehan et al. The yarn has a particular structure from being entangled in the entangling apparatus.

U.S. Pat. No. 4,152,885 to Cox, Jr., describes an interlocked yarn wherein at least one of the individual filaments in the bundle encircles the other filaments to interlock the filaments together. The yarn is made by feeding the filament bundle into a fluid medium flowing opposite of the direction of bundle travel.

U.S. Pat. No. 4,152,886 to Nelson describes a yarn which is intermittently debulked by passing a stream of heated gas through the yarn while it is under tension. The process achieves varying levels of bulking and debulking.

U.S. Pat. No. 4,697,317 to Nelson is directed to a randomly-spaced, tightly entangled nub yarn and the process and apparatus for making the same. As a starting point, the process uses crimped and interlaced supply yarn. Nelson uses the term "nub" to denote what is referred to herein as a hard node. According to this Nelson patent, the nubs can be up to 1 inch (2.54 cm) long.

Although the above patents often result in filaments with node spacing such as the even node spacing produced by the rotary wheel interlacer of U.S. Pat. No. 3,110,151, such node spacing is not an answer to the problem of stria caused by nodeless gaps. As an illustration, exactly even node spacing can result in patterning in some carpet constructions which resembles that experienced from the twist cabled ends of multicolored bulked continuous filament (BCF).

A further problem encountered in producing interlaced yarn which is suitable for applications requiring uniformity, such as carpet applications, is that air entangling conditions which are severe enough to insure regular nodes also produce excessively tight nodes. These hard nodes, like the "nubs" of Nelson, reduce carpet yarn cover in carpet applications, give the carpet a harsh hand and also make tufting difficult. Thus soft node yarn is desirable for both mixed fiber and unmixed (homogeneous) fiber yarns. For homogeneous yarns, soft nodes maintain consistent coherence without sacrificing cover with hard knots, or affecting the carpet tufting by nubbiness in the face or picks from hard nodes in the tufting needles.

Previously known means to soften the nodes result in undesirable effects. For example, reduction of fluid flow rate or increased process speed causes unacceptably irregular spacing between nodes which can, as noted, cause streaking due to stria. On the other hand, at a given fluid flow rate, slowing down the process speed makes the nodes harder and also limits production rate. Reducing the yarn tension can cause a high degree of yarn fuzziness which then interferes with further handling like tufting. Also, low tensions make consistency difficult to maintain and the process difficult to control.

In the development of interlaced yarns having desirable properties discussed above for intended end uses, it has been problematic to quantify the entanglement characteristics. Thus, there remains a need for methods to so characterize the yarns.

SUMMARY OF THE INVENTION

Accordingly, the present invention relates to a method for quantifying interlacing characteristics of multifilamentary yarn, having nodes of a length and a width. The method includes the steps of
(a) measuring the length (L) of at least one node;
(b) measuring the width (W) of at least each node measured in step (a);
(c) determining the value of the node harshness from the ratio of L to W for each node measured in step (a).

It is an object of the present invention to provide an improved test method for nodally entangled multifilamentary yarn.

Related objects and advantages will be apparent to one ordinarily skilled in the relevant art after reviewing the following description.

DESCRIPTION OF THE PREFERRED EMBODIMENTS

For the purposes of promoting an understanding of the principles of the invention, reference will now be made to specific embodiments of the invention and specific language which will be used to describe the same. It will nevertheless be understood that no limitation of the scope of the invention is thereby intended, such alterations and further modifications, and such further applications of the principles of the invention as discussed are contemplated as would normally occur to one skilled in the art to which the invention relates.

An easily discernible difference between the harshness of soft nodes and hard nodes can be felt by pulling the respective yarns between the thumb and forefinger of a human hand. Yarn harshness is, however, a fairly qualitative characteristic which has, to some extent, eluded quantitative definition. The present invention addresses this in a novel method for determining the harshness of entangled yarn relative to the hardness or softness of the nodes is set forth herein. The difference between soft and hard nodes is quantified by what is hereafter referred to as The Yarn Harshness Test.

Figures 1, 2, 3:
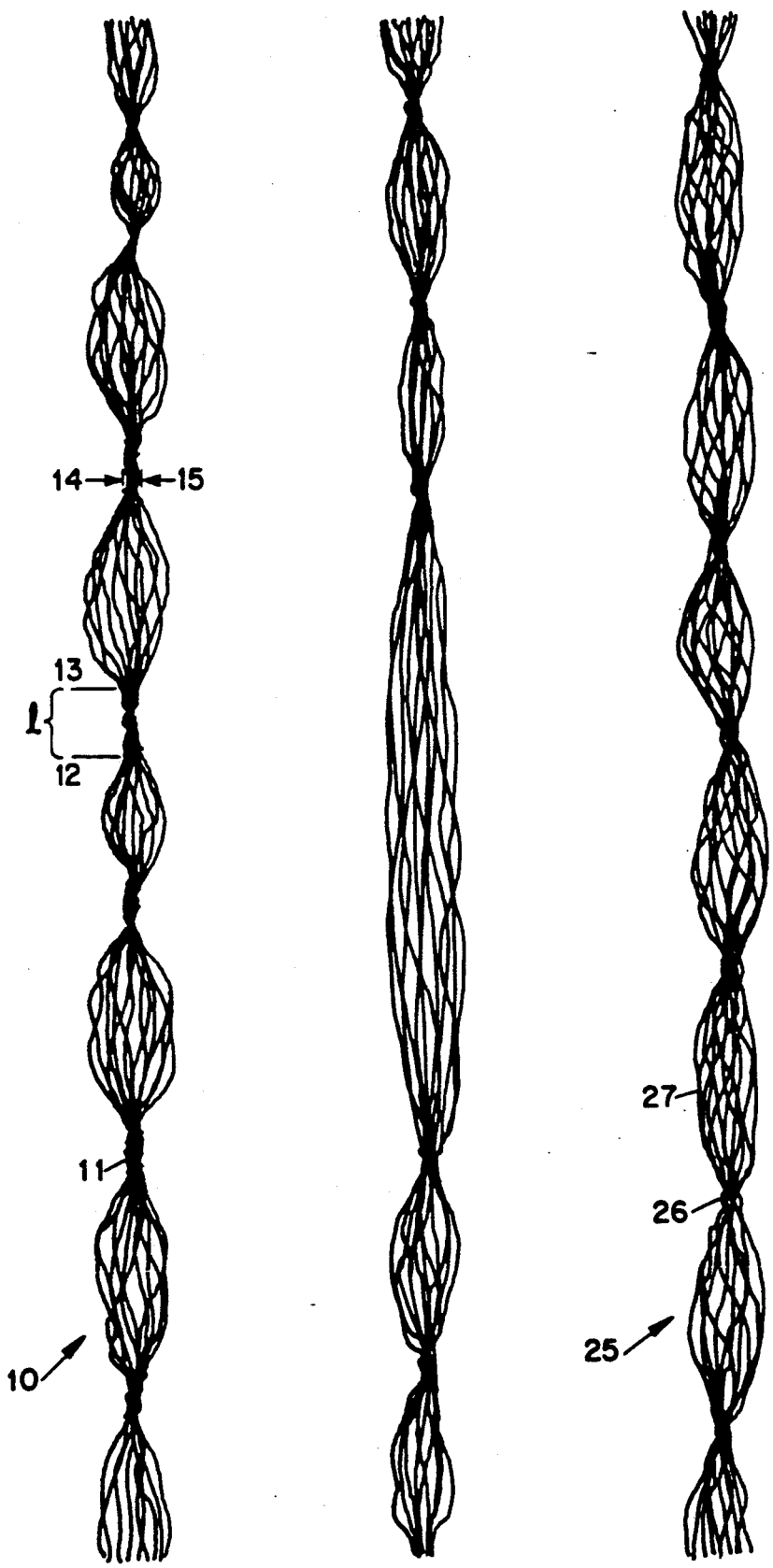
FIG. 1 is a schematic view of harsh yarn having hard nodes.
FIG. 2 is a schematic view of irregular yarn having unacceptably large nodeless gaps.
FIG. 3 is a schematic view of soft yarn having soft regularly spaced nodes.

In The Yarn Harshness Test, a value is assigned to the ratio of the node length to the width or diameter. This ratio is referred to as the node harshness. Lower numbers indicate softer nodes. Node dimensions can be determined with, for example, a calibrated microscope or a pocket scope. With reference to FIG. 1, yarn 10 is shown having nodes 11. Node length (L) is defined as the space between the beginning 12 of nodal entanglement and the end 13 of nodal entanglement. Node width (W) is defined, for the present purposes, as the distance between top 14 of a node shown in the orientation of FIG. 1 and bottom 15 of that node. For accuracy, a number of nodes are assigned a harshness and the average harshness determined. In most cases, nodes in any yarn will be an approximately Gaussian distribution of harshness. The average of node harshness correlates to carpet hand, yarn cover and tufting performance and provides a comparison factor with respect to these properties for yarns having equal numbers of nodes per meter. To assign Yarn Harshness, the number of nodes per meter is multiplied by the average individual node harshness. Visual counting is one method to determine nodes per meter.

Yarns with large gaps or unentagled sections such as that illustrated in FIG. 2 may yield low yarn harshness numbers. These yarns may tuft and feel like the soft node product but are unlikely to yield satisfactory carpet uniformity if different filaments are used in individual yarns. Therefore, a Standard Yarn Streak Potential Test may be used as a second factor to determine the suitability of yarns for specified end uses. The Standard Yarn Streak Potential Test is described in U.S. Pat. No. 4,894,894 to Coons, III et al. which is hereby incorporated by reference for the Standard Yarn Streak Potential Test defined therein. This test can be used to estimate yarn uniformity by measuring the yarn DL. DL is a measurement of the color space value or lightness or darkness of a sample compared to a standard. The measurement sytem, CIE L*a*b*, was developed by the International Commission on Illumination. The standard used in the Standard Yarn Streak Potential Test is established from an average of readings on the standard sample. Then the standard deviation of a chosen sample's observed DL is compared against the averaged standard to give a reliable quantitive estimate of striations in the sample when tufted and overall propensity of a yarn to streak in full width carpet.

As an aid to understanding the present invention reference is now made to the invention of commonly owned U.S. patent application, Ser. No. 07/619,377. A first embodiment of that invention relates to a yarn having a low yarn harshness and, where the yarn is made of mixed filaments, a low streak potential. FIG. 3 illustrates yarn 25 of this first embodiment. Yarn 25 has what is referred to herein as soft nodes 26. These soft nodes are characterized by an average node harshness of no more than about 2.0 which yields a Yarn Harshness of no more than about 100. The gaps are spaced approximately, although not necessarily exactly, uniformly with internodal spacings of no more than about 6 cms. Where the yarn is made of mixed filaments, uniformity in the final yarn use is insured if the differential lightness (DL) standard deviation remains less than about 6 as determined by the Standard Yarn Streak Potential Test.

Figure 4:
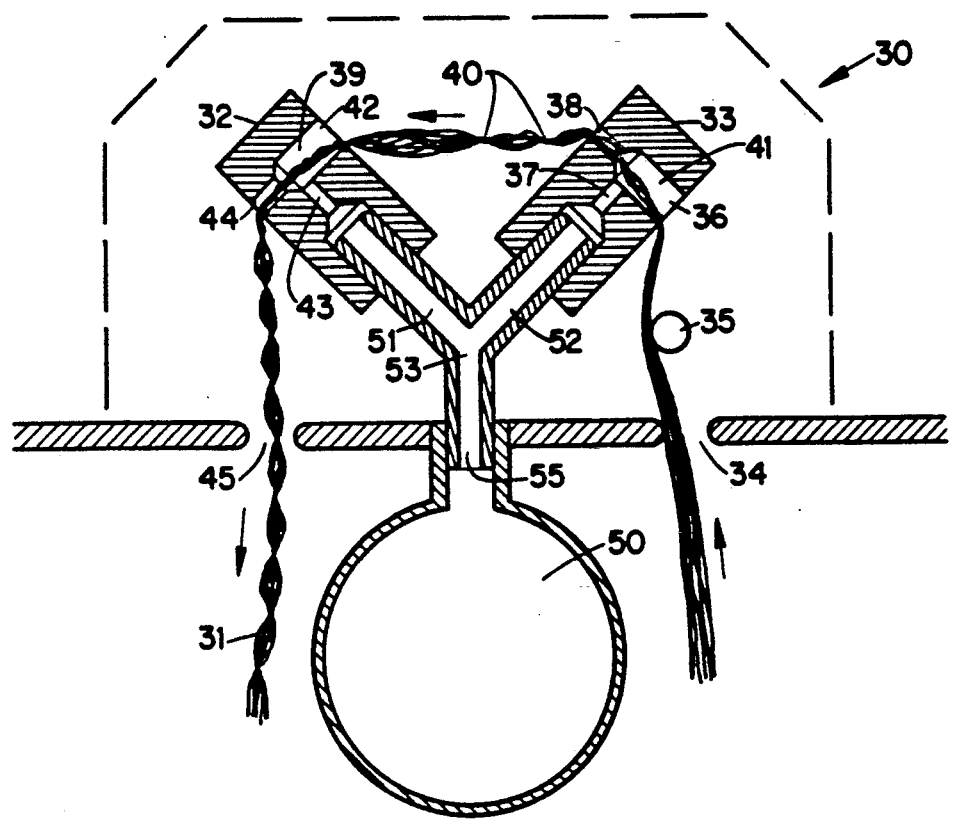
FIG. 4 is a side plan view of an apparatus shown with a first interlacer design.

A second embodiment of that invention relates to an apparatus for interlacing the yarn in the method of the present invention. Interlacing apparatus 30 is illustrated in FIG. 4. The apparatus can be used in nearly any air entangling process that normally results in tight nodes. Exemplary processes are described in U.S. Pat. No. 4,223,520 to Whitted et al. and U.S. Pat. No. 4,570,312 to Whitener, Jr. Even entangling processes that have nearly the opposite goal, i.e., preparation of compact or hard nodes, may benefit when the apparatus is used. Two examples of these processes are U.S. Pat. No. 4,064,686 to Whitted et al. and U.S. Pat. No. 4,152,886 to Nelson. In all of these processes, the apparatus is used by substituting for the interlacer called for therein.

Turning now to apparatus 30 in more detail, FIG. 4 shows apparatus 30 installed with the apparatus of the process disclosed in U.S. Pat. No. 4,570,312 to Whitener, Jr. That patent is hereby incorporated by reference for the process taught therein and for purposes of illustrating how the present apparatus may by used in interlacing operations. It will be recognized that the illustration of the apparatus with the process of U.S. Pat. No. 4,570,312 is not intended to limit the scope of the invention but is intended to enhance its understanding. As shown, apparatus 30 is mounted on housing 29 in the position of the interlacing head and includes interlacers 32 and 33 arranged in series. One suitable interlacer for use in the present apparatus is described in U.S. Pat. No. 4,841,606 to Coons, III, which is hereby incorporated by reference as an example of a useful interlacer. (See FIG. 5.) Guide pin 35 is optional. Each interlacer 32 and 33 includes a yarn passageway 39 and 41, respectively, and air jet/orifice inlet 43 and 37, respectively. Air jet/orifice inlets 43 and 37 are connected to air supply 50 through conduits 51 and 52, respectively. Yarn passageways 39 and 41 include yarn inlets 42 and 36, respectively, and yarn outlets 44 and 38 in continuous communication therewith.

Yarn 31 is shown moving through a set of interlacers 32 and 33 in the direction of the arrows. Untangled multifilamentary yarn enters interlacing apparatus 30 through apparatus feed port 34 and may contact pin 35, if pin 35 is present. The yarn then enters the inlet port 36 of interlacer 33 where yarn 31 is subjected to a stream of forced fluid. The fluid enters yarn passageway 41 at air inlet 37. The action of the fluid causes entangling of the yarn. The yarn then exits first interlacer 33 through outlet port 38. As shown, the action of first interlacer 33 results in the formation of random nodes 40.

Continuing in its path, yarn 31 then enters second interlacer 32 through its yarn inlet 42 where yarn 31 is subjected to fluid impingement in yarn passageway 39 through inlet 43. Yarn 31 then exits second interlacer 32 through yarn outlet 44. As a result, additional nodes 46 are formed in portions of yarn 31 left unentangled by first interlacer 33. For this reason, the interlacers should operate independently. Yarn 31 then exits interlacing apparatus 30 through apparatus exit port 45.

Fluid is supplied to interlacers 32 and 33 from fluid supply 50. Air is one suitable fluid. Conduits 51 and 52 supply a predetermined fluid pressure to respective interlacers 32 and 33 As shown, individual conduits 51 and 52 may join so that after junction 53 they form a main fluid supply conduit 55.

For maximum effectiveness, interlacer 32 and interlacer 33 should be arranged to operate independently. This means that the action of first interlacer 33 will not interfere with the interlacing action of second interlacer 32. In the illustration of FIG. 4, because of the effectiveness of the total interlacing action, each interlacer is supplied with relatively low air flow/pressure. Where the interlacer of U.S. Pat. No. 4,841,606 is used, the instant apparatus obtains enhanced efficiency. The notches present in the yarn passageway of that interlacer guide the yarn into the region of fluid impingement. It is contemplated that any interlacer having means to guide the yarn into the fluid jet will achieve some degree of improved efficiency over interlacers which allow the yarn to move freely through the cross section of the interlacer. The interlacers should preferably be aligned with the air orifice or jet perpendicular to the thread path. The yarn most preferably passes directly over the air jet (43 and 37 in FIG. 4). It is presently believed that interlacers which operate based on free movement of the yarn in the entanglement chamber like that taught in Bunting, Jr., can not be used advantageously herein.

The overall air usage with two (2) interlacers is only slightly higher than with that of a single interlacer. The optimum air pressure varies according to yarn speed and denier. For example, the following air pressures are suitable under the conditions: 3,000 denier-55 psig; 4,000 denier-70 psig; 5,000 denier-85 psig; and 6,000 denier-100 psig at 750 yds/min.

Air pressure is adjusted for yarn denier and physical properties. In the absence of adjustable air pressure, the interlacer units can be equipped with various jet orifice sizes for yarn denier and physical properties. The first interlacer, as noted, makes many nodes but leaves gaps. The second interlacer is, of course, not effective where nodes already exist. It adds nodes only where the first interlacer left gaps. It should be noted that more than two independent interlacers could be used to further insure that no exceptionally large gaps pass through and cause yarn having unsuitably high streak potential.

The arrangement of the two (2) independent interlacers must not create excessive yarn tension, as high tension can pull soft nodes into hard nodes. Accordingly, the interlacers are arranged to provide yarn angling for efficient interlacer operation with tension high enough to make the process controllable without fuzziness but below a tension which causes hard nodes. In this regard, the portion of the yarn passageway within each interlacer should be oriented to operate nearly completely independently, for example, between about 90° and about 120° with reference to the longitudinal axes of the passageways. For instance, the longitudinal axes interlacers 32 and 33 of FIG. 4 are oriented in an approximately 90° angle. Presently, it is considered most preferable if the yarn enters and leaves each interlacer at an angle of about 45° for a total yarn angle of 180° (from feed port 34 to exit port 45 in the variation of FIG. 4).

Figure 5:
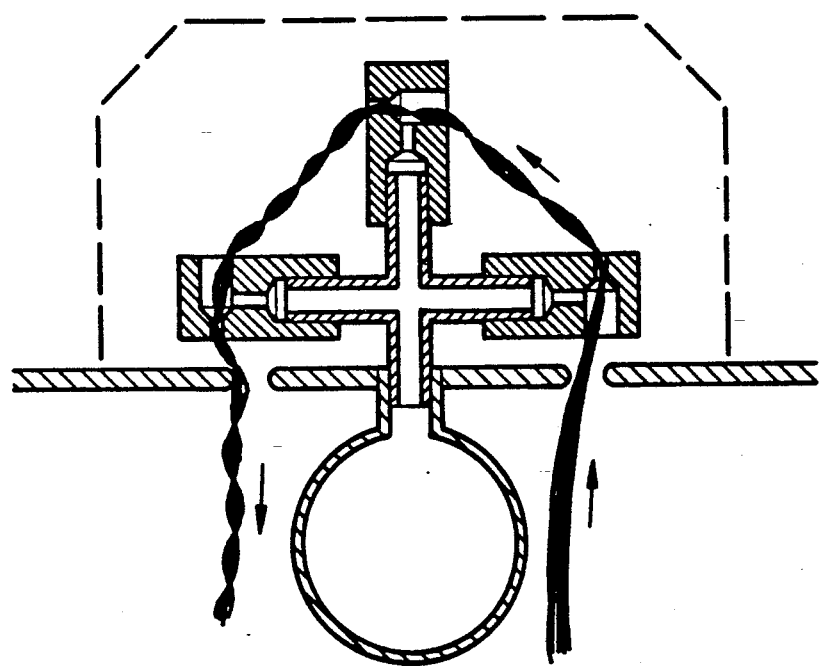
FIG. 5 is an alternate interlacer arrangement.

In the variation of FIG. 5 showing three interlacers, the longitudinal axis of the yarn passageway of each interlacer preferably remains about 90° (as illustrated). The yarn enters and leaves each interlacer preferably at an angle of about 45° for a total yarn angle of about 180°, i.e., the yarn reverses the direction of travel in going through the apparatus.

Figure 6:
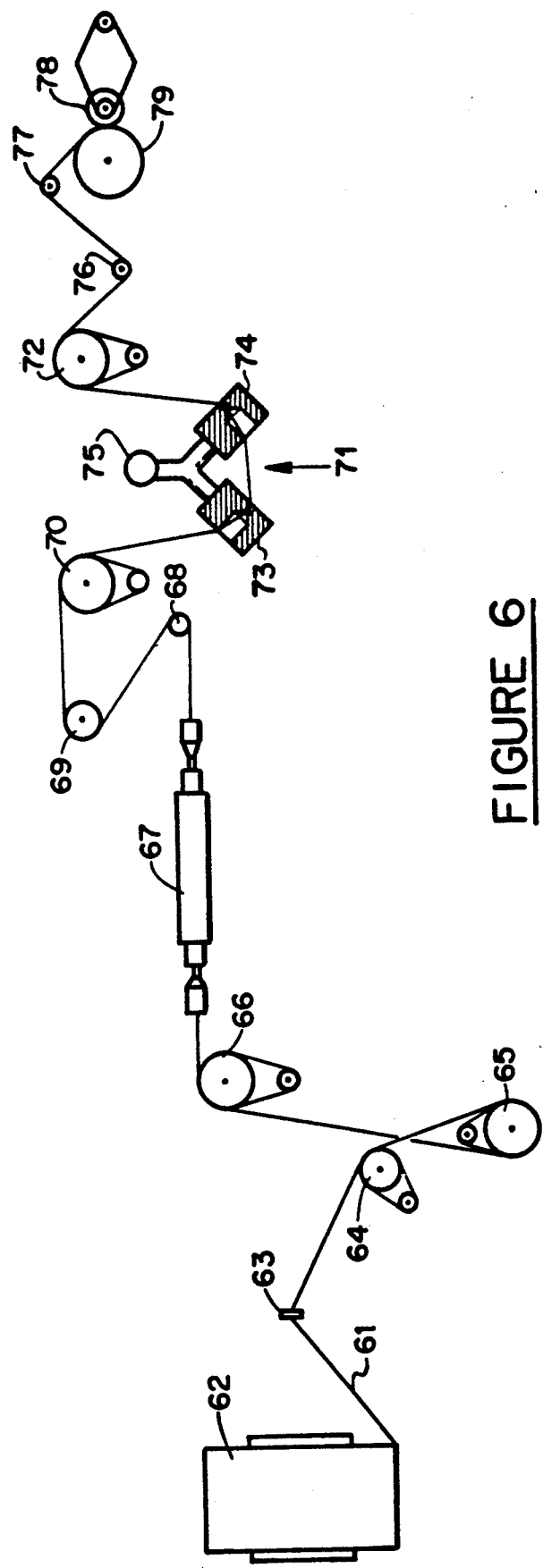
FIG. 6 is a side plan view of an apparatus shown with a second interlacer design and adapted for concurrent drawing and bulking.

A further variation concerns the provision of an additional mechanism for concurrently drawing (orienting) and bulking (crimping) the yarn. This modification is exemplified in Example 2. Advantageously, by combining the drawing and bulking steps with entangling, the product yarn is more economical to make. Previously, processes which similarly combined steps were very limited by the speed at which effective entangling and blending of the multicolored filaments could be insured. Furthermore, the combination of this variation with air obviates expensive, messy and dangerous steam. One manner of carrying out this modification is illustrated in FIG. 6. For the following description, reference is made to U.S. Pat. No. 4,894,894 which has previously been incorporated by reference for the Streak Potential Test taught therein and which is now hereby incorporated by reference for the process and apparatus taught therein. In general, the drawing and bulking take place as described in the patent, but with the entangling apparatus discussed herein substituted for the intermixing jet taught therein.

Illustrated in FIG. 6 is a schematic which is exemplary of an apparatus according to the variation of the second embodiment wherein the yarn is concurrently drawn, bulked and analyzed. Undrawn feed yarn 61 is taken off of package 62, fed through first guide 63 and makes about three wraps around first godet 64. First godet 64 is used to pretension the yarn. The yarn is then drawn between second godet 65 and third godet 66. The yarn makes seven or eight wraps around both second godet 65 and third godet 66. Yarn 61, now drawn, is then bulked in tube 67. One useful tube is described in U.S. Pat. No. 3,908,248. Now bulked yarn 61 then travels over direction changing roll 68 and tension device 69 after which the yarn contacts a fourth godet 70 and a fifth godet 72. The bulked yarn is overfed from fourth godet 70 to fifth godet 72. Between these godets (70 and 72) is situated the interlacer apparatus 71 of the present invention. As shown, interlacer apparatus 71 includes two interlacers (shown in partial cross section to illustrate the shape of the yarn passageway therethrough and in communication with interlacers 73 and 74 and air supply 75. After exiting the fifth godet, yarn 61 passes over another direction changing roller 76 and onto tranverse rolls 77 of a winder. Yarn package 78 is then built up Package 78 is driven by friction roll 79. In this manner the final yarn is entangled, drawn and bulked in a single integrated process. The yarn produced has superior streak resistance (when made of multicolored filaments or filaments with different dye affinities) and increased processibility from the presence of soft nodes.

A third embodiment is a process for preparing soft node yarn. This process involves subjecting a multifilamentary yarn to a first interlacing jet followed by subjecting the yarn to a second interlacing jet which operates completely independently of the first jet. This process results in yarn having a node harshness of less than about 2.0. One such process, which is presently preferred, is described above in connection with the apparatus of the second embodiment. The process may include the drawing step, for example, as accomplished with the apparatus shown schematically in FIG. 6.

The invention will now be further described by reference to the following more detailed examples. The examples are set forth by way of illustration only and are not intended to limit the scope of the invention.

EXAMPLE 1

The method described herein is useful to evaluate entangled yarn and predict its performance in level loop carpet. Yarn according to the following table was evaluated according to the present invention. The results are summarized in Table I.

TABLE I

|  | YARN A | YARN B |
| --- | --- | --- |
| Yarn type | Nylon 6 BCF* | Nylon 6 BCF* |
| Yarn denier | 3,345 | 3,345 |
| Yarn filaments | 174 | 174 |
| Filament cross section | Trilobal | Trilobal |
| Node harshness: |  |  |
| avg of 30 | 1.8 | 3.6 |
| std dev | 0.9 | 1.2 |
| Nodes per meter: |  |  |
| avg of 3 meters (visual count) | 46 | 49 |
| Yarn harshness | 83 | 176 |
| Level Loop Carpet-28 oz/yd$^2$, 1/10 guage |  |  |
| Tufting face picks/5 yd$^2$ | 0 | 3 |
| Carpet surface texture | Even | Uneven |
| Carpet surface hand | Smooth | Rough |
| Level Loop Carpet-20 oz/yd$^2$, 1/10 guage |  |  |
| Carpet backing visable | No | Yes |

*Bulked continuous filament

What is claimed is:

1. A method for preparing multifilamentary yarn having a yarn harshness of no more than about 100 comprising the steps of:
   a) passing multifilamentary yarn nonlinearly through a sequential tandem interlacing jet wherein fluid is jetted under pressure at a rate to each jet, thereby preparing a first interlaced multifilamentary yarn having nodal entanglement of a length and width, said preparing including operating each interlacing jet independently of the action of the other interlacing jet;
   b) quantifying the nodal entanglement of the first yarn by measuring the length and width of the nodal entanglement for at least one node, determining a ratio of length to width, for each nodal entaglement measured and assigning the ratio as a node harshness value;
   c) when the node harshness is more than about 2, adjusting the relative position of said jets and the rate and pressure of fluid jetting; and
   d) repeating steps a), b) and c) until the node harshness value is no more than about 2.

2. The method of claim 1 wherein said quantifying includes assigning a node harshness for at least two nodes is a strand of yarn; and averaging the resulting determined node harshness to arrive at an average node harshness.

3. The method of claim 2, wherein said quantifying further includes counting the number of nodes in a meter of yarn; and multiplying the counted number by the average node harshness to determine yarn harshness;

said adjusting includes, when said yarn harshness is more than about 100, adjusting the relative position of the jets and the rate and pressure of fluid jetting; and and said repeating includes repeating steps (a), (b) and c until said yarn harshness is no more than about 100.

4. The method of claim 3 wherein the number of nodes in at least two predetermined lengths is individually counted and average individual count is calculated and used for said multiplying.

* * * * *